(12) United States Patent
Faccioli et al.

(10) Patent No.: US 8,690,419 B2
(45) Date of Patent: Apr. 8, 2014

(54) CARTRIDGE FOR STORAGE AND DELIVERY OF A TWO-PHASE COMPOUND

(75) Inventors: Giovanni Faccioli, Monzambano (IT); Renzo Soffiatti, Nogara (IT)

(73) Assignee: Tecres S.p.A., Sommacampagna (VR) (IT)

( * ) Notice: Subject to any disclaimer, the term of this patent is extended or adjusted under 35 U.S.C. 154(b) by 851 days.

(21) Appl. No.: 11/920,638

(22) PCT Filed: Jan. 27, 2006

(86) PCT No.: PCT/IB2006/000148
§ 371 (c)(1),
(2), (4) Date: Nov. 28, 2007

(87) PCT Pub. No.: WO2006/123205
PCT Pub. Date: Nov. 23, 2006

(65) Prior Publication Data
US 2008/0312588 A1    Dec. 18, 2008

(30) Foreign Application Priority Data

Oct. 12, 2007  (IT) .............................. VI2005A0152

(51) Int. Cl.
| | | |
|---|---|---|
| *B01F 13/06* | (2006.01) | |
| *B01F 13/00* | (2006.01) | |
| *B67D 7/70* | (2010.01) | |
| *B65D 25/08* | (2006.01) | |

(52) U.S. Cl.
USPC ............ 366/139; 366/130; 222/137; 206/222

(58) Field of Classification Search
USPC ................. 206/219, 222; 366/189, 139, 130; 604/87, 88; 222/137
See application file for complete search history.

(56) References Cited

U.S. PATENT DOCUMENTS

| | | | | |
|---|---|---|---|---|
| 2,490,552 | A * | 12/1949 | Smith ............................. | 604/88 |
| 3,489,147 | A * | 1/1970 | Shaw ............................... | 604/88 |
| 3,659,749 | A * | 5/1972 | Schwartz ....................... | 222/129 |
| 3,756,390 | A * | 9/1973 | Abbey et al. .................. | 206/219 |
| 3,785,379 | A * | 1/1974 | Cohen ............................. | 604/88 |
| 3,840,136 | A * | 10/1974 | Lanfranconi et al. ............. | 215/6 |
| 4,676,657 | A * | 6/1987 | Botrie ........................ | 366/181.5 |
| 4,886,495 | A * | 12/1989 | Reynolds ........................ | 604/88 |
| 4,983,164 | A * | 1/1991 | Hook et al. ..................... | 604/87 |
| 4,998,927 | A * | 3/1991 | Vaillancourt ................. | 604/537 |
| 5,032,117 | A * | 7/1991 | Motta .............................. | 604/88 |
| 5,114,240 | A * | 5/1992 | Kindt-Larsen et al. ........ | 366/129 |

(Continued)

FOREIGN PATENT DOCUMENTS

EP                397589 A1 * 11/1990 ................ B01F 3/12

*Primary Examiner* — Tony G Soohoo
*Assistant Examiner* — Anshu Bhatia
(74) *Attorney, Agent, or Firm* — Tutunjian & Bitetto P.C.

(57) ABSTRACT

This invention finds application in the field of the devices and methods for physical or chemical mixing of products and particularly relates to a cartridge for storage and sterile delivery of a two-phase compound. The cartridge comprises a first tubular member (2) which defines a first chamber (3) for storage of a solid phase, having a bottom wall (6) with an opening (7) for the passage of the compound, a second tubular member (9) which defines a second hermetically sealed chamber (12) for storage of a liquid phase, and a piston which sealably slides within the first tubular member (2), means (8) for occluding said opening (7) which comprise at least one rupturable membrane (15) associated to the bottom wall (6).

19 Claims, 4 Drawing Sheets

(56) References Cited

U.S. PATENT DOCUMENTS

| | | | |
|---|---|---|---|
| 5,114,421 A | 5/1992 | Polak | |
| 5,364,369 A * | 11/1994 | Reynolds | 604/187 |
| 5,429,603 A * | 7/1995 | Morris | 604/88 |
| 5,435,645 A | 7/1995 | Faccioli et al. | |
| 5,586,821 A * | 12/1996 | Bonitati et al. | 366/139 |
| 5,588,745 A | 12/1996 | Tanaka et al. | |
| 5,921,419 A * | 7/1999 | Niedospial, Jr. et al. | 215/247 |
| 5,971,181 A * | 10/1999 | Niedospial et al. | 215/247 |
| 6,017,349 A * | 1/2000 | Heller et al. | 606/92 |
| 6,039,718 A * | 3/2000 | Niedospial, Jr. | 604/408 |
| 6,349,850 B1 * | 2/2002 | Cheikh | 222/1 |
| 6,406,175 B1 | 6/2002 | Marino | |
| 6,902,543 B1 * | 6/2005 | Cherif-Cheikh et al. | 604/82 |
| 7,018,089 B2 * | 3/2006 | Wenz et al. | 366/130 |
| 7,073,936 B1 * | 7/2006 | Jonsson | 366/139 |
| 2001/0034527 A1 * | 10/2001 | Scribner et al. | 606/93 |
| 2003/0040701 A1 * | 2/2003 | Dalmose | 604/87 |
| 2004/0066706 A1 * | 4/2004 | Barker et al. | 366/139 |
| 2005/0148992 A1 * | 7/2005 | Simas et al. | 604/403 |
| 2006/0164913 A1 * | 7/2006 | Arramon | 366/139 |

* cited by examiner

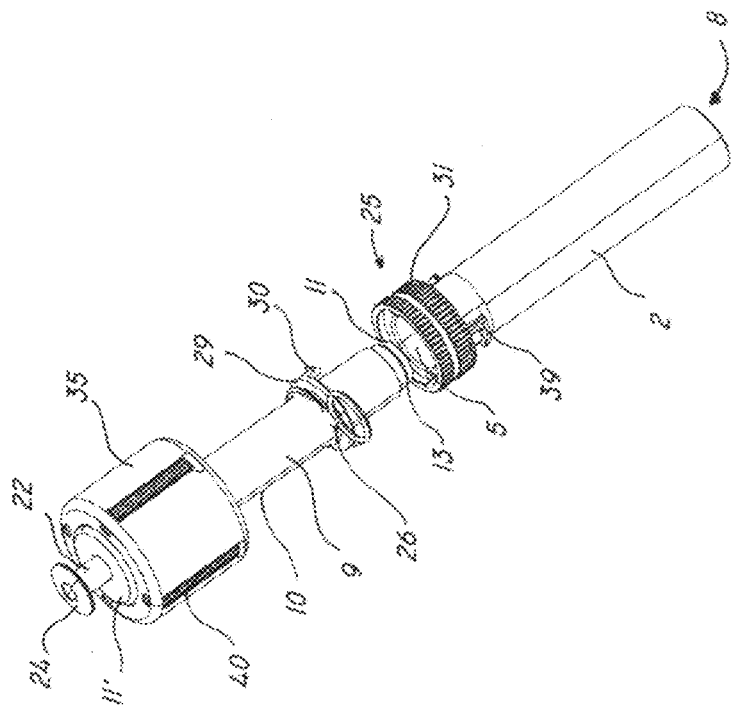
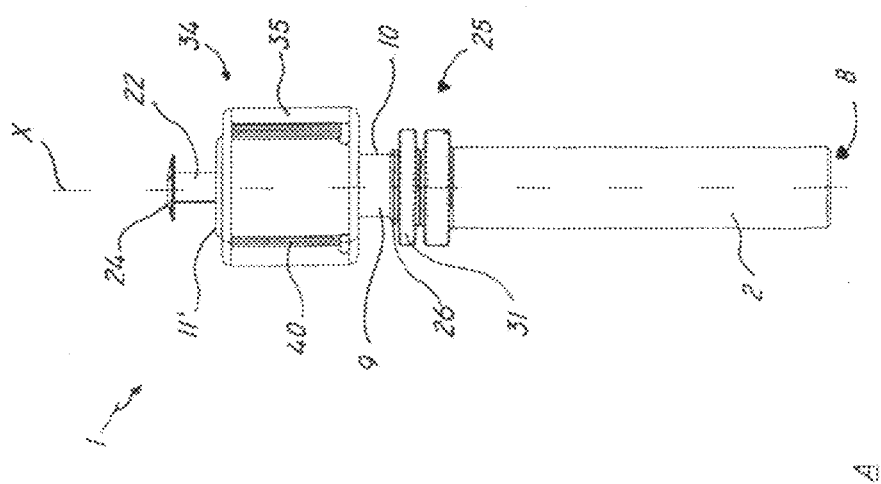
FIG. 2
FIG. 1

CARTRIDGE FOR STORAGE AND DELIVERY OF A TWO-PHASE COMPOUND

FIELD OF THE INVENTION

This invention finds application in the field of the devices and methods for physical or chemical mixing of products, and particularly relates to a cartridge for storage and sterile delivery of a two-phase compound.

BACKGROUND OF THE INVENTION

As is known, arthroplasty surgery, and particularly vertebroplasty operations require an appropriate amount of material to be introduced in the specific area to be treated to reinforce the implant site.

Therefore, invasive procedures such as percutaneous vertebroplasty or the like interventions, aimed for example at reducing vertebral compressions, require materials having the highest biological and microbiological safety and compatibility with the human body.

The currently used materials in this branch of surgery include specific acrylic resins, usually composed of a generally monomeric liquid component, which is used as a solvent for polymerization of a powder.

The two components are first enclosed in two separate containers, and later premixed to be introduced in the bone or vertebral cavity to be treated.

The liquid is held in a suitable container, such as a plastic bag or a glass vial. This later must withstand the chemical action of the liquid contained therein and must further have adequate mechanical strength and sealing properties, due to the toxicity of commonly used monomers.

Later, as the container is opened, the liquid is poured into a container in which the powder was previously placed, and is mixed therewith.

The latter step is typically carried out by an operator by means of a paddle, which may be operated manually or though a suitable container cover, equipped with a paddle rotating arrangement.

The compound so obtained is finally introduced in a special delivery syringe and pressure injected into the bone cavity for implantation through a special needle.

These prior art solutions have the recognized drawback of exposing the operator with a highly reactive and toxic liquid, whose vapors may be freely released in the work environment, and be potentially inhaled by the operator. Also several steps are provided in which the bone cement is in contact with the outside environment. This can easily affect cement sterility whereby the cement may be an infection carrier for the patient being treated.

Furthermore, the preparation and the percentage composition of the mixture strongly depends on the particular skill of the operator, whereby there is the risk of obtaining cements that are not perfectly homogeneous or with the two phases in improper proportions.

A further drawback of these typical solutions is that the cement delivery pressure is exerted directly by the operator, thus resulting in a very low pressure. Hence, low-viscosity cements have to be used, whereas the medullary material has a much higher density.

In an attempt to overcome the above drawbacks, a number of different solutions have been provided, in which one or more of such drawbacks have been obviated.

U.S. Pat. No. 5,435,645, in the name of the same applicant, and WO-01/83094 disclose bone cement mixing devices, in which cement is prepared in sterile conditions. The liquid is first placed in a first chamber and later forced into a second chamber that contains the powder. Finally, the two phases are mixed by mechanical stirring. This further provides a cement having proper monomer and powder proportions.

Nevertheless, a drawback of these solutions is that the cement so obtained has to be still poured into a suitable delivery system, other than the device. This is a critical step of the process, as it is necessarily carried out in non-sterile conditions and as such can be a possible cause of contamination for the operator and the work environment.

SUMMARY OF THE INVENTION

The object of this invention is to overcome the above drawbacks, by providing a cartridge for storage and sterile delivery of a two-phase compound that is highly efficient and cost-effective.

A particular object is to provide a cartridge that allows mixing, storage and delivery of a two-phase compound in absolutely sterile conditions.

A further object is to provide a device that eliminates any risk of contamination for the operators and the work environment in the steps of compound preparation and implantation.

Furthermore, a particular step is to provide a cartridge that allows component mixing and compound delivery steps to be carried out in a simple and safe manner.

An additional object of the invention is to provide a cartridge that can be interfaced directly and in a simple and stable manner with an external device for delivery or direct placement of the compound.

These and other objects that will be more apparent hereinafter, are fulfilled by a cartridge for storage and sterile delivery of a two-phase compound which includes a first tubular member which defines a first chamber for storage of the solid phase, the first chamber having a first side wall with an open end and a bottom wall with an opening for the passage of the resin, means for occluding the opening, and a second tubular member which defines a second chamber for storage of a liquid phase, and sealably slides within the first tubular member.

According to the invention, the occlusion means comprise at least one frangible membrane associated to the bottom wall of the first tubular member, and designed to be associated, at said occlusion means, with external means for delivery and direct implantation of the compound in absolutely sterile conditions and particularly with high pressure delivery means.

Thanks to this particular arrangement, the cartridge of the invention allows to mix the components and store the compound thereby obtained in absolutely sterile conditions. Furthermore, the possible coupling of the cartridge to the compound delivery means can avoid any contact of the compound with the outside environment and preserve the sterility of the process.

Conveniently, the occlusion means may comprise a cylindrical conduit coaxial to the first tubular member, for bringing the first chamber in fluid communication with the external resin implantation means.

Preferably, the cylindrical conduit may have a compound inlet at the bottom wall, and an opposite outlet, and the frangible membrane will be situated downstream from the inlet.

Thanks to this particular arrangement, the cartridge may be directly and simply interfaced with an external device for direct placement of the resin or with an additional interface for resin delivery to such external device.

Furthermore, the occlusion means may include a non-return valve which is engageable in the cylindrical conduit and may be associated to the first end wall of the second tubular member.

This will prevent the latter from moving upwards into the first chamber, when pushed by the external delivery means during compound delivery.

Advantageously, means may be provided for selective attachment of the first tubular member to the second tubular member, in such a manner as to make the piston susceptible of sliding or not in the first chamber thereby defining a negative pressure therein, so as to facilitate the ingress of the liquid phase.

Preferably, the attachment means may include a selective abutment member, which may be removably connected to the second tubular member.

Also, the attachment means may include a flange for integral connection to the piston, which has at least one substantially longitudinal projection.

Furthermore, the attachment means may include a cylindrical ring, coaxial to the first member, which may have at least one recess therein for snap engagement with the projection of the connection flange, to connect the first and the second tubular members together.

This particular arrangement allows to control the movement of the piston and to prevent it from moving within the first chamber before the liquid phase container has been ruptured, and later to prevent it from being fully extracted from the first member during vacuum generation, which makes each step simpler and safer.

Conveniently, the second tubular member may have means for removable connection to external resin implantation means.

Preferably, the first side wall of the first chamber may have at least one receptacle formed therein for the mixed compound, with the cartridge being connected to the external delivery means and with the first end wall of the piston at least partly in contact with the bottom wall of the first chamber.

Thus, the interface between the cartridge and the external means will have an even added safety and stability, thereby increasing sterility during resin delivery.

BRIEF DESCRIPTION OF THE DRAWINGS

Further features and advantages of the invention will be more apparent from the detailed description of a preferred, non-exclusive embodiment of a cartridge for storage and sterile delivery of a two-phase compound according to the invention, which is described by way of non-limiting example with the assistance of the annexed drawings, in which:

FIG. 1 is a front view of the cartridge according to the invention;

FIG. 2 is an exploded view of the cartridge of FIG. 1;

DETAILED DESCRIPTION OF A PREFERRED EMBODIMENT

Referring to the above figures, a cartridge for storage and sterile delivery of a two-phase compound, particularly an acrylic resin or a bone cement for use in arthroplasty or vertebroplasty, is generally designated by numeral 1 and particularly shown in FIG. 1.

The resin may be composed of a generally monomeric liquid phase, and a solid phase in powder form, possibly added with antibiotic or growth-promoting agents, which polymerizes in solution in the liquid phase. The two phases are first separated, with the liquid phase being preferably stored in a frangible container F, such as a commonly used glass vial. According to an additional embodiment, the compound may also be a drug selected from the group consisting of antibiotics, vitamins or the like.

Figure 3:
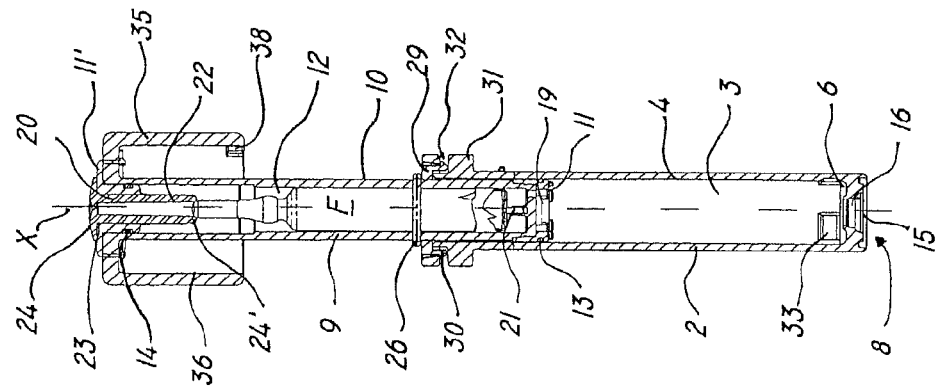
FIG. 3 is a sectional view of the cartridge of FIG. 1 as taken along the plane I-I, in a first operating configuration.

As particularly shown in FIG. 2 and FIG. 3, the cartridge is composed of a first tubular member 2, extending in a substantially longitudinal direction along an axis X. The member 2 defines a first chamber 3 with a first side wall 4 having an open end 5 and a bottom wall 6 and in which the solid component is designed to be contained in sterile conditions. The bottom wall 6 has an opening 7, through which the resin is to be delivered, once the phases have been mixed.

In a first configuration A, as shown in FIG. 1, the opening 7 is closed by suitable occlusion means 8 associated to the bottom wall 6, which allow steril storage of the resin. The cartridge 1 further comprises a second tubular member 9 with a second side wall 10, a first and a second end walls 11, 11', defining a second hermetically sealed chamber 12, in which the liquid phase of the resin will be held in sterile conditions. The second tubular member 9 is configured to define a piston to be inserted in the first tubular member 2, to sealably slide therein.

The second tubular member 9 will be arranged to slide in a sealing manner by using a seal 13 in external contact with the second side wall 10 of the second tubular member 9 and in the proximity of the first end wall 11 thereof. The tightness of the second chamber 12 may be provided by an O-ring 14 located internally thereof at its second end wall 11'.

In the first operating arrangement A, the piston 9 may be held in the first tubular member 2 so that about one half of its length is contained therein, without wholly engaging the first chamber 3.

Figure 5:
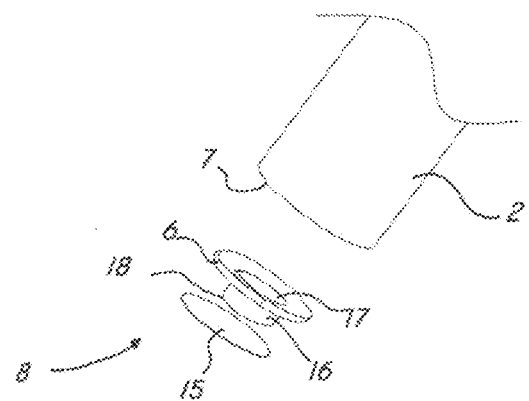
FIG. 5 is an exploded view of a first detail of FIG. 1.

According to the invention, the occlusion means 8 include at least one rupturable membrane 15, particularly shown in FIG. 5, which is associated to the bottom wall 6 of the first chamber 3 and the second tubular member 9 may be associated, at such occlusion means 8, to external means E for "on site" implantation of the resin in absolutely sterile conditions.

The membrane 15 may be disc-shaped and made of a non porous material such as aluminum or the like, and may be connected to the first member 2 by a heat sealing process to be carried out before introducing the solid phase in the first chamber 3.

Later, the whole cartridge 1 may be sterilized with a hot or cold sterilization process. The cartridge may be made of a rigid or semi-rigid transparent plastic material and may be of the disposable type.

The occlusion means 8, as shown in FIG. 5, may advantageously comprise a cylindrical conduit 16 coaxial to the first tubular member 2, which is designed to brig the first chamber 3 in fluid communication with the external resin implantation means E. Therefore, the conduit 16 has an inlet 17 communicating with the opening 7 of the bottom wall 6 of the first chamber 3 and an outlet 18, which is occluded by the membrane 15 before delivery.

Figure 6:
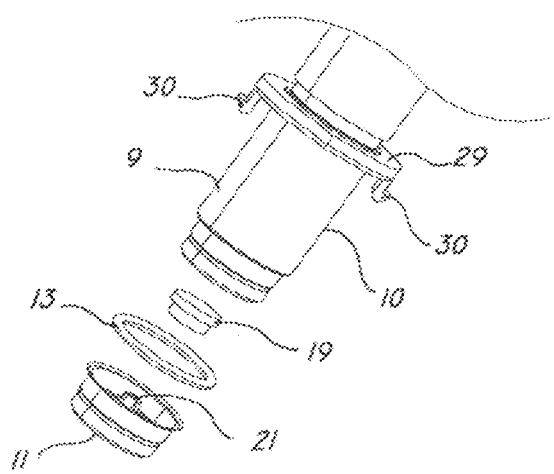
FIG. 6 is an exploded view of a second detail of FIG. 1.

In this particular arrangement, a non-return valve 19, as shown in FIG. 6, may be associated to the first end wall 11 of the piston 9, and will engage the cylindrical conduit 16 as soon as the piston 9 will reach the end of its stroke in the first chamber 3. Thus, the resin will be prevented from moving back upwards in the first chamber 3 during resin implantation. The valve 19 may be made of silicone or another similar material.

Figure 4:
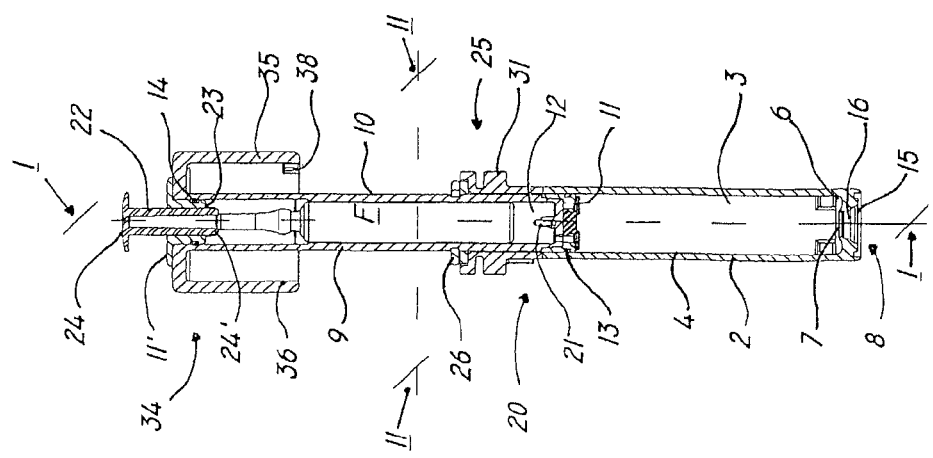
FIG. 4 is a sectional view of the cartridge of FIG. 1 as taken along the plane I-I, in a second operating configuration.

Conveniently, as shown in FIGS. 3 and 4, the second chamber 12 may be configured in such a manner as to be able to hold the storage container F of the liquid phase. The chamber 12 may further contain suitable means 20 for rupturing the container F and allow the liquid phase therein to be released.

Advantageously, the rupturing means 20 may include a pointed element 21, situated at the first end wall 11 of the second tubular member 9, and a cylindrical member 22, which is slidably housed in a through hole 23 formed in the second end wall 11' of the same member 9. The cylindrical member 22 has an end 24 that is operable from the outside, whereas the opposite end 24' comes in contact with the container F and pushes it against the pointed element 21 to cause rupturing thereof.

Suitably, the cartridge 1 may have means 25 for selectively attaching the piston 9 to the first tubular member 2 to control the movement of the piston 9.

Preferably, the attachment means 25 may include a selective abutment member 26, which may be removably connected to the second tubular member 9. The element 26 will be present until rupture of the container F to prevent the piston 9 from sliding within the first chamber 3 before such rupture. The element 26 may be configured as an open ring attached to a hook, to facilitate removal, and may be made of a flexible plastic material.

Thus, the passage of liquid from the second chamber 12 into the first chamber 3 will occur as the piston 9 slides in the first tubular member 2 alternately in the two opposite directions of the longitudinal axis X. Consequently, a negative pressure will be generated in the first chamber 3 for the solid phase, to facilitate the passage of the latter into the liquid phase.

Figure 7:
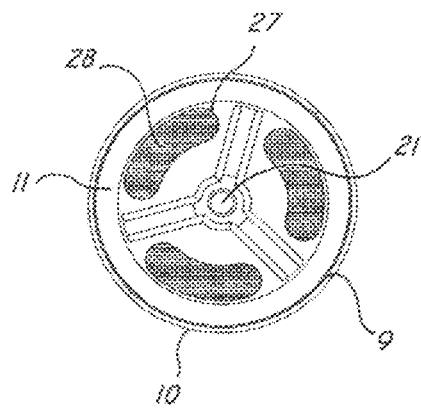
FIG. 7 is a sectional view of the detail of FIG. 6 as taken along a plane II-II.

As shown in FIG. 7, the first end wall 11 of the piston 9 may have a plurality of through recesses 27, arranged symmetrically to the axis X, to facilitate the passage of the liquid.

Advantageously, the recesses 27 may be at least partly occluded by a filter 28, to allow that only liquid flow into the first chamber 3. This will prevent glass fragments of the vial F from reaching the first chamber 3 and the solid component from being sucked back into the second chamber 12 as vacuum is generated in the first chamber 3.

Once the liquid phase has passed into the first chamber 3, the whole cartridge 1 will be shaken for a predetermined and known minimum time, until a resin ready for implantation is obtained.

Furthermore, the attachment means 25 may include a connecting flange 29 which is mounted to the piston 9 and has a pair of projections 30 arranged symmetrically to the longitudinal axis X.

Also, the attachment means 25 may include a cylindrical ring 31 unitary with the first member 2, on which two recesses 32 may be arranged symmetrically to the axis X. Each recess 32 may be snap engaged by a respective projection 30 of the flange 29 to prevent the piston 9 from coming out of the first chamber 3 during vacuum generation.

Once the components have been mixed together and the resin so obtained is ready for implantation, the piston 9 may be operated to push the resin from the first chamber 3 into a resin implantation device or into an intermediate bone cement storage and delivery device D, thereby maintaining absolute sterile conditions in each operating phase.

Conveniently, seats 33 may be formed inside the first side wall 4 of the first chamber 3, to enable the contact of the first end wall 11 of the piston 9 with the bottom wall 6 of the first chamber 3, particularly when the chamber is connected with the intermediate device D. In this case, an enhanced stability of such connection may be obtained by rotating the cartridge 1 relative to the device D. This movement will require a further extrusion of the resin which will pass through seats 33 to escape and facilitate the operation thereby reducing the efforts required of the operator.

Figure 9:
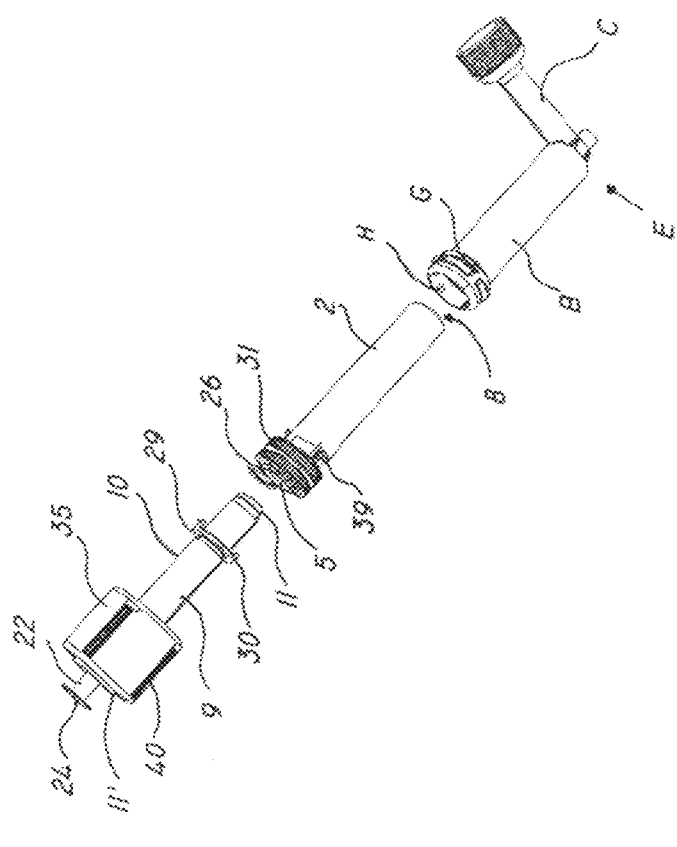
FIG. 9 is an exploded view of FIG. 8.
Figure 8:
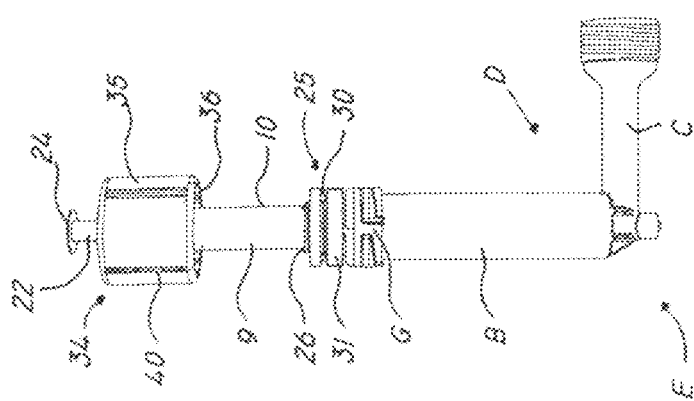
FIG. 8 is a perspective view of the invention in a particular combination with external compound delivery means.

FIGS. 8 and 9 show, for illustration purposes, a particular external resin delivery device D that can interface with the cartridge 1 to connect it to a second external resin implantation device.

The external device D may have, for instance, a first cylindrical sleeve B to be associated to the cartridge 1, in which means are provided for rupturing the membrane 15. Thus a fluid communication can be established between the first chamber 3, that contains the resin ready for implantation and a second sleeve C which may be connected to a common device for high pressure delivery to the implantation device, which devices are not shown, because of common use.

Finally, the cartridge 1 may conveniently have means 34 for removable connection to external resin delivery means E.

In a preferred, non-exclusive embodiment of the invention, the connection means 34 may comprise a cylindrical element 35 coaxial to the second member 9, and formed of one piece with the second end wall 11' thereof. The side wall 36 of the element 35 may further have an internal tooth element 38 at its bottom end, for engaging a groove G possibly formed on the outer wall of the first cylindrical sleeve B of the external resin delivery device D. The first tubular member 2 may further have two outer ridges 39 for interacting with corresponding notches H formed in the inner wall of the first cylindrical sleeve B.

Therefore, the relative sliding motion of the tooth 38 in the groove G and the ridges 39 in the notches H will provide a removable connection between the cartridge 1 and the external means E. The cylindrical element 36 may further have a plurality of outer longitudinal grooves 40, to improve the grip on the device D by the operator, thus enhancing the stability of the connection.

In view of the foregoing, it is apparent that the cartridge of the invention fulfils the proposed objects, and particularly provides a cartridge that allows mixing and delivery of a two-phase compound in absolutely sterile conditions, while eliminating any risk of contamination for the operators and the work environment, during preparation and direct implantation of the compound.

Furthermore, the particular configuration of the means for occluding the opening of the first chamber, allows the cartridge to be directly interfaced with an external device for direct delivery of the compound.

The cartridge of the invention is susceptible of a number of modifications and changes all falling within the scope of the appended claims. All the details thereof may be replaced by other technically equivalent parts, and the materials may vary depending on different needs, without departure from the object of the invention.

While the cartridge has been described with particular reference to the accompanying figures, the numerals referred to in the disclosure and claims are only used for the sake of a better intelligibility of the invention and shall not be intended to limit the claimed scope in any manner.

The invention claimed is:

1. A cartridge for storage and sterile delivery of a two-phase compound, composed of a liquid phase and a solid phase which are mixed together in said cartridge immediately before delivery of said compound, comprising:

a first tubular member which defines a first chamber for storage of said solid phase, with a first side wall having an open end and a bottom wall, said first tubular member defining a longitudinal axis;

a second tubular member with a second side wall, a first and a second end walls, defining a second hermetically sealed chamber for storage of said liquid phase, said second hermetically sealed chamber forming with said first chamber a hermetically sealed space in said cartridge for the storing and mixing of said liquid and solid phases, said second tubular member defining a piston which sealably slides within said first tubular member for extrusion of said compound, the bottom wall of said first tubular member having an opening for the passage of the compound to be delivered from said cartridge; and occlusion means for occluding said opening;

wherein said occlusion means comprise a non-return valve to permit flow of the compound in one direction and at least one rupturable membrane which is coupled to said bottom wall, wherein said first tubular means is configured to receive an external delivery means at said occlusion means, whereby the membrane may be ruptured without the compound contacting an outside environment, for delivery from said cartridge and direct implantation of said compound in absolutely sterile conditions.

2. The cartridge as claimed in claim 1, wherein said membrane is ruptured by a rupturing means provided in said external delivery means.

3. The cartridge as claimed in claim 1, wherein said occlusion means comprise a cylindrical conduit coaxial to said first member, said cylindrical conduit being engageable with the non-return valve associated to said first end wall of said second tubular member.

4. The cartridge as claimed in claim 3, wherein said cylindrical conduit has an inlet and an outlet for the compound, said inlet being situated at said bottom wall, said at least one rupturable membrane being placed downstream from said inlet.

5. The cartridge as claimed in claim 1, wherein said second side wall of said piston has a seal coaxial to said second member, said seal being situated at said first end wall of said second member.

6. The cartridge as claimed in claim 1, including a liquid phase container, said second tubular member comprising means for rupturing said container in said second chamber.

7. The cartridge as claimed in claim 6, wherein said rupturing means include a pointed element at said first end wall of said second tubular member.

8. The cartridge as claimed in claim 7, wherein said rupturing means include a cylindrical member, which slides in a through hole formed in said second end wall of said second tubular member, said cylindrical member having an end that is operable from the outside whereas the opposite end is adapted to interact with said container to push it against said pointed element.

9. The cartridge as claimed in claim 1, wherein said first end wall of said second tubular member has at least one through recess to put said first and second chambers in fluid communication.

10. The cartridge as claimed in claim 9, wherein said at least one through recess is at least partly occluded by a filter.

11. The cartridge as claimed in claim 1, including means for selective attachment of said first and second tubular members, in such a manner as to make said piston susceptible of sliding in said first chamber thereby defining a negative pressure therein, so as to facilitate the ingress of the liquid phase into said first chamber.

12. The cartridge as claimed in claim 11, wherein said attachment means comprise a selective abutment element which is removably engageable onto said second tubular member.

13. The cartridge as claimed in claim 11, wherein said attachment means comprise a flange for integral connection to said piston, said flange having at least one substantially longitudinal projection.

14. The cartridge as claimed in claim 13, wherein said attachment means comprise a cylindrical ring coaxial to said first member, said cylindrical ring having at least one recess therein for snap engagement with said at least one projection of said connection flange.

15. The cartridge as claimed in claim 1, including means for removable connection to said external delivery means.

16. The cartridge as claimed in claim 1, wherein said first chamber has at least one seat for the passage of the compound delivered from said cartridge when connected to the external delivery means.

17. The cartridge as claimed in claim 1, wherein said external delivery means are connected to means for delivering the compound at high pressure.

18. The cartridge as claimed in claim 1, wherein said at least one rupturable membrane consists of an aluminum disc which is heat sealed to the bottom wall of the first tubular member.

19. A cartridge for storage and sterile delivery of a two-phase compound, composed of a liquid phase and a solid phase which are mixed together in said cartridge immediately before delivery of said compound, comprising:

a first tubular member which defines a first chamber for storage of said solid phase, with a first side wall having an open end and a bottom wall, said first tubular member defining a longitudinal axis;

a second tubular member with a second side wall, a first and a second end walls, defining a second hermetically sealed chamber for storage of said liquid phase, said second hermetically sealed chamber forming with said first chamber a hermetically sealed space in said cartridge for the storing and mixing of said liquid and solid phases, said second tubular member defining a piston which sealably slides within said first tubular member for extrusion of said compound, the bottom wall of said first tubular member having an opening for the passage of the compound to be delivered from said cartridge; and occlusion means for occluding said opening;

wherein said occlusion means comprise at least one rupturable membrane which is coupled to said bottom wall, wherein said first tubular means is suitable to be coupled at said occlusion means with external delivery means, whereby the membrane may be ruptured without the compound contacting an outside environment, for delivery from said cartridge and direct implantation of said compound in absolutely sterile conditions.

* * * * *